US006939998B2

United States Patent
Satek et al.

(10) Patent No.: US 6,939,998 B2
(45) Date of Patent: Sep. 6, 2005

(54) PREPARATION OF 5-TERT-BUTYL-METAXYLENE USING A SOLID ACTIVE CLAY CATALYST

(75) Inventors: Larry C. Satek, Fremont, IN (US); Stephen C. Jevne, Wheaton, IL (US); Surjit S. Chhatwal, Downers Grove, IL (US)

(73) Assignee: The University of Southern Mississippi Research Foundation, Hattiesburg, MS (US)

( * ) Notice: Subject to any disclaimer, the term of this patent is extended or adjusted under 35 U.S.C. 154(b) by 23 days.

(21) Appl. No.: 10/657,802

(22) Filed: Sep. 8, 2003

(65) Prior Publication Data

US 2004/0152934 A1 Aug. 5, 2004

Related U.S. Application Data

(60) Provisional application No. 60/408,715, filed on Sep. 6, 2002.

(51) Int. Cl.$^7$ .................................................. C07C 2/68
(52) U.S. Cl. ....................................................... 585/468
(58) Field of Search .......................................... 585/468

(56) References Cited

U.S. PATENT DOCUMENTS

| 3,284,523 | A |  | 11/1966 | Beck et al. |  |
|---|---|---|---|---|---|
| 3,379,787 | A |  | 4/1968 | Amir |  |
| 3,849,507 | A | * | 11/1974 | Zuech | 585/455 |
| 4,551,573 | A |  | 11/1985 | Cobb |  |
| 6,271,298 | B1 | * | 8/2001 | Powell | 524/445 |

FOREIGN PATENT DOCUMENTS

| GB | 1 227 419 | 4/1971 |
|---|---|---|
| JP | 3024021 | 1/1991 |

OTHER PUBLICATIONS

Article by Ghosh, Swapan Kumar; Sharma, Man Mohan published in Ind. Eng. Chem. Res., dated 1992; vol. 31, No. 1; pp. 445–449 entitled Separation of m– and p–xylene via selective alkylation/dealkylation—transalkylation.

* cited by examiner

Primary Examiner—Thuan Dinh Dang
(74) Attorney, Agent, or Firm—Welsh & Katz, Ltd.

(57) ABSTRACT

Alkylation of metaxylene with isobutylene using a solid active clay catalyst produces 5-tert-butyl-metaxylene with high isomer selectivity with respect to 4-tert-butyl-metaxylene. The process is controlled to extend catalyst life and significantly reduce environmentally unfriendly waste.

17 Claims, 2 Drawing Sheets

PREPARATION OF 5-TERT-BUTYL-METAXYLENE USING A SOLID ACTIVE CLAY CATALYST

This application claims the benefit of provisional No. 60/408,715 filed Sep. 6, 2002.

FIELD OF THE INVENTION

This invention is directed to the production of 5-tert-butyl-metaxylene by the alkylation of metaxylene with an alkylating agent using a solid active clay catalyst. This invention is also directed to a continuous commercial process for producing 5-tert-butyl-metaxylene by the alkylation of metaxylene with an alkylating agent using a solid active clay catalyst.

BACKGROUND OF THE INVENTION 5-tert-butyl-metaxylene (5tBuMX) is a necessary feedstock in the production of tert-butyl-isophthalic acid and other intermediates in the production of industrial chemicals. 5tBuMX is generally produced by the alkylation of metaxylene with isobutylene using a catalyst.

Catalysts commonly used in the production of 5tBuMX are aluminum halides, strong acids and hydrogen fluoride. U.S. Pat. No. 3,379,787 to Amir discloses the alkylation of $C_8$ aromatic hydrocarbon with diisobutylene or trilsobutylene and using anhydrous aluminum chloride liquid as a catalyst. U.S. Pat. No. 4,551,573 to Cobb discloses addition of elemental iodine to improve alkylation of aromatic compounds using an aluminum halide catalyst. U.S. Pat. No. 3,284,523 to Beck et al. discloses a method for the production of 5tBuMX by alkylation of metaxylene using a sulfuric acid catalyst. Great Britain Patent No. 1,227,419 to Japan Gas Co. discloses the use of a hydrogen fluoride catalyst.

Use of aluminum halide catalysts results in low yield. Strong acid catalysts provide poor selectivity for the 5tBuMX Isomer, and a significant amount of 4tBuMX is created which must be separated from the 5tBuMX isomer. The toxicity of hydrogen fluoride makes it very difficult to handle. Currently, catalysts are used In a liquid or gas phase. Separating the catalyst from the reaction products is difficult. Additionally, catalysts currently used in the art result in environmentally unfriendly waste products. There is a need for a method to produce 5tBuMX with sufficient yield and high selectivity while using a catalyst that can be easily separated from the reaction products and results in less waste material and where the waste material is environmentally benign.

Ghosh discloses use of a solid acid montmorillonite clay catalyst in separation of metaxylene and paraxylene. Separation Through Reactions, Dept. of Chemical Technology, University of Bombay, September 1991. Japanese Patent No. 03024021 to Fujita, et al. discloses use of an active clay catalyst for production of 5tBuMX by the alkylation of metaxylene with isobutylene. Use of an active clay catalyst results in higher conversion of isobutylene but less than 50% conversion of metaxylene. Active clay catalyst also shows high selectivity for 5tBuMX, and can be separated from reaction products by known methods such as filtration. Unfortunately, use of clay catalyst in accordance with the disclosure of Fujita et al. results in unacceptably rapid deactivation of the clay catalyst. Rapid deactivation of clay catalyst and low metaxylene conversion result in excessive waste, much of which is environmentally harmful. Additionally, large scale production of 5tBuMX in accordance with the disclosure of Fujita et al. would consume excessive amounts of clay catalyst and metaxylene thereby making its large-scale use unfeasible. There is a need for a process for the production of 5tBuMX using a solid catalyst that maximizes catalyst life, maximizes isobutylene conversion, provides high selectivity for the 5tBuMX isomer, and minimizes waste product.

SUMMARY OF THE INVENTION

A process to produce 5-tert-butyl-metaxylene comprises: the steps of adding a suitable alkylating agent to a mixture comprising active clay catalyst and an effective amount of metaxylene into a reactor at reaction conditions comprising a temperature of at least 125° C. and a pressure of at least 450 kPa at an alkylating agent addition rate effective to form 5-tert-butyl-metaxylene; recovering a portion of the 5-tert-butyl-metaxylene and a portion of the metaxylene; separating the 5-tert-butyl-metaxylene from the metaxylene; and recycling at least a portion of the separated metaxylene to the reactor.

BRIEF DESCRIPTION OF THE DRAWING

FIG. 1 is a process diagram representing the alkylation process through the catalyst extraction.

FIG. 2 is a process diagram representing the purification steps of the process.

DESCRIPTION OF THE PREFERRED EMBODIMENT(S)

Figure 1:
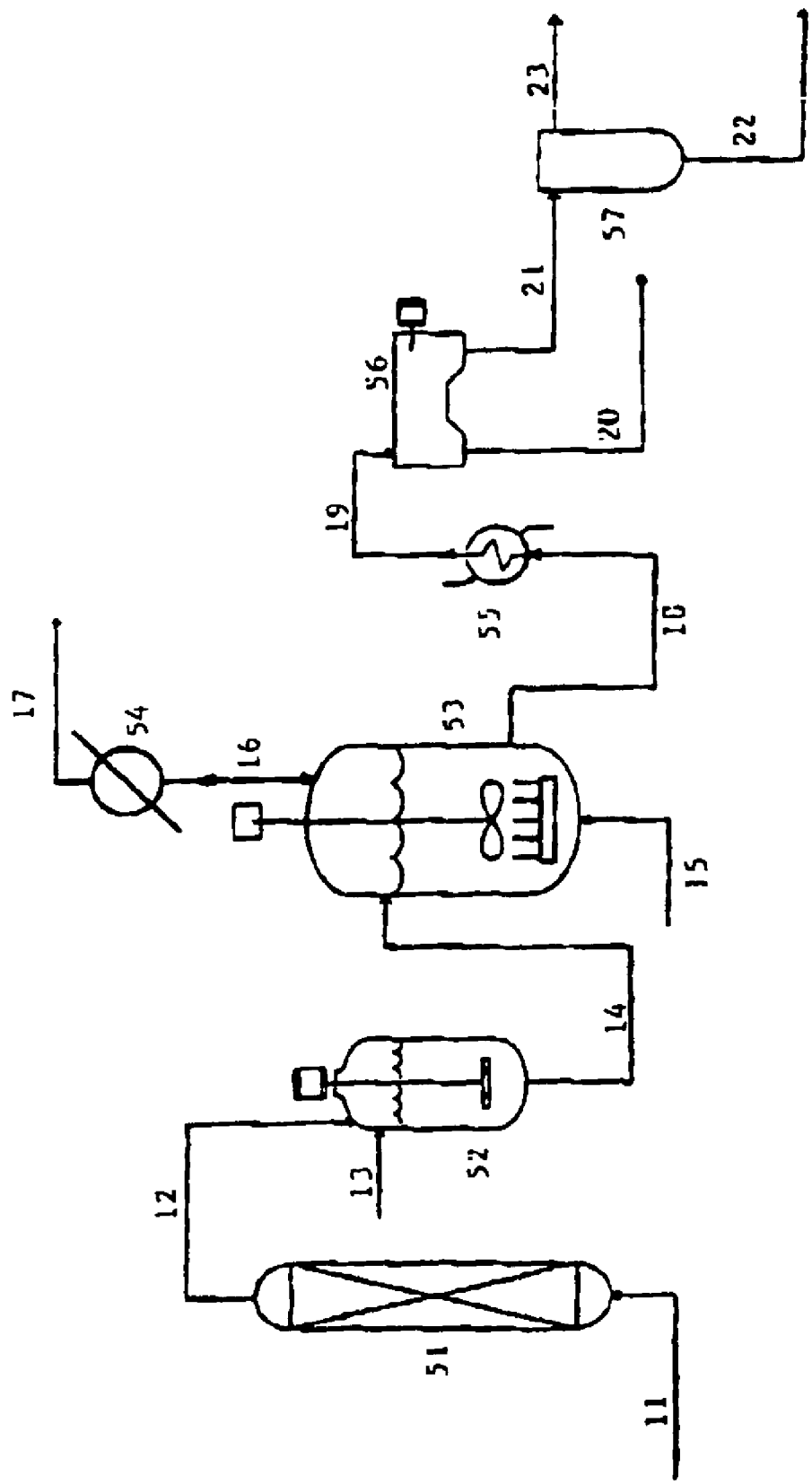
FIGS. 1 and 2 are flow sheets illustrating one embodiment of this invention.

This invention relates to a process for producing 5tBuMX by the alkylation of metaxylene with isobutylene using a solid active clay catalyst (the "clay catalyst"). As used in this specification and in the succeeding claims, the term 'clay' refers generally to aluminosilicates having particle size in the micron range and having a layered molecular arrangement. The term 'active clay' refers generally to clay which has been treated to increase its Bronsted acidity. Typically, clays are activated by treatment with concentrated mineral acids, for example, sulfuric, hydrochloric, and phosphoric acids.

Processes currently used in the art for producing 5tBuMX from metaxylene have significant disadvantages including difficulty separating catalyst from reaction product and poor selectivity for the 5tBuMX isomer. Current processes also generate waste products which are difficult to handle and which require costly disposal methods. A clay catalyst is much easier to remove from reaction products, and provides high selectivity, but it also results in lower metaxylene conversion leading to excessive waste. Also, clay catalysts have been found to have short lifetimes. Short catalyst lifetime and excessive waste of both metaxylene and clay catalyst have rendered use of a clay catalyst in a commercial process unfeasible. It has unexpectedly been discovered that clay catalyst life can be greatly extended thereby reducing catalyst waste and making use of a clay catalyst possible for commercial processes. It has also been discovered that metaxylene can be recycled without significant loss in process effectiveness thereby reducing metaxylene waste. A continuous recycle process was additionally discovered for commercial use of a clay catalyst in the production of 5tBuMX.

This invention can be a batch process but is preferably a continuous process. The clay catalyst of this invention is a solid active clay catalyst. The clay used for the clay catalyst is typically a smectite clay, more preferably a dioctahedral smectite clay. Most preferably the clay used for the clay catalyst is a montmorillonite clay. The clay is then activated to prepare it for use as the clay catalyst. Clay catalysts of this invention can be purchased commercially. For example, FILTROL 24 ("F-24") can be purchased from Englehard.

Clay catalyst is mixed in a vessel with an effective amount of metaxylene. An effective amount of metaxylene is an amount allowing sufficient excess of metaxylene in the alkylation process to promote the desired alkylation reaction and inhibit formation of byproducts. A sufficient excess of metaxylene is relative to both the alkylating agent and the clay catalyst. Having a sufficient excess of metaxylene will vary with the particular process conditions and the desired production rate and quality. Generally, having a sufficient excess of metaxylene will require a weight ratio of metaxylene to catalyst of at least 4:1. For typical operations, the weight ratio of metaxylene to clay catalyst should be from about 5:1 to about 19:1. Preferably, the weight ratio of metaxylene to clay catalyst is about 9:1.

The vessel is maintained at a pressure greater than about 460 kPa. The actual pressure used will be at least partly determined by the specific structure and arrangement of the process equipment, but typically, the vessel is operated at a pressure of from about 515 kPa psig to about 620 kPa. Preferably, the vessel is operated at a pressure of about 585 kPa. Vessel pressure is typically achieved by adding nitrogen, however, other non-reactive gases can be used.

Vessel temperature will vary with the process equipment used and the operating pressure, but generally, vessel temperature is at least about 125° C. Preferably vessel temperature is maintained at from about 131° C. to about 156° C. Most preferably vessel temperature should be about 135° C.

A suitable alkylating is then added to the vessel at a rate effective to form 5-tert-butyl-metaxylene. A suitable alkylating agent is one that is capable of adding a t-butyl group to the "5-position" of metaxylene. For purposes of this invention, the term "isobutylene" includes isobutylene and its dimer and trimer forms such as diisobutylene and tri-isobutylene. Effective rate is a rate sufficient to produce the desired amount of 5tBuMX while minimizing undesirable side reactions. Effective rate will vary depending upon the operating conditions, size, and shape of the vessel. Effective rate will also depend upon the quantity of metaxylene in the vessel and upon the method used to introduce the alkylating agent into the vessel. The effective rate will be greater if greater quantities of metaxylene and clay catalyst are used, however, dispersion of the alkylating agent will be a limiting factor for increase in effective rate. By reducing localized concentrations of alkylating agent, dispersion of the alkylating agent reduces the occurrence of side reactions when compared to introducing an alkylating agent without appreciable dispersion. In general, effective rate will be greater if the alkylating agent is well dispersed when compared to effective rate when the alkylating agent is poorly dispersed. Dispersion methods can include using multiple sites to add alkylating agent, using dispersion apparatus such as a multi-ring disperser, and includes any method or apparatus capable of reducing localized concentrations of alkylating agent.

The effective rate for adding alkylating agent is specified relative to the amount of metaxylene in the vessel. For typical operations, the effective rate should be no greater than about 0.35 g/min for every 100 g of metaxylene in the vessel. Preferably, the effective rate is in the range of from about 0.11 g/min to about 0.35 g/min for every 100 g of metaxylene in the vessel. More preferably the effective rate is from about 0.13 g/min to about 0.29 g/min for every 100 g of metaxylene in the vessel. The vessel contents can be mixed to improve the alkylation reaction and decrease oligomerization of alkylating agent molecules. If performed as a batch process, the alkylating agent is typically added for about 100 minutes before the reaction is terminated. It has been found that this process of producing 5tBuMX unexpectedly results in greatly extended catalyst life. The life of the clay catalyst is increased from 2 to 3 uses to at least 11 uses in batch operation with limited loss of catalytic activity.

In another embodiment of the instant invention, a clay catalyst feed is mixed with an effective amount of metaxylene from a metaxylene feed to form a slurry feed. The slurry feed can be formed in a slurry tank or by any other mixing means. An effective amount of metaxylene is an amount allowing sufficient excess of metaxylene in the alkylation process to promote the desired alkylation reaction and inhibit formation of byproducts. A sufficient excess of metaxylene is relative to both the alkylating agent and the clay catalyst. A sufficient excess of metaxylene will vary with the particular process conditions and the desired production rate and quality. Generally, having a sufficient excess of metaxylene will require a weight ratio of metaxylene to catalyst in the slurry feed of at least 4:1. For typical continuous operations, the weight ratio of metaxylene, to clay catalyst in the slurry feed should be from about 5:1 to about 19:1. Preferably, the weight ratio of metaxylene to clay catalyst is about 9:1.

The slurry feed is then fed to an alkylation reactor. The reactor is maintained at a pressure greater than about 450 kPa. The actual pressure used will be at least partly determined by the specific structure and arrangement of the process equipment, but typically, the reactor is operated at a pressure of from about 515 kPa to about 620 kPa. Preferably, the reactor is operated at a pressure of about 585 kPa. Reactor pressure can achieved by adding nitrogen, other non-reactive gases or other methods practiced in the art.

Reactor temperature will vary with the process equipment used and the operating pressure, but generally, reactor temperature is at least about 125° C. Preferably reactor temperature is maintained at from about 131° C. to about 156° C. Most preferably reactor temperature should be about 135° C. The slurry feed is preferably at or near reactor temperature before entering the reactor, however, the slurry can be heated in the reactor.

A suitable alkylating agent is then added to the reactor at an effective rate Effective rate is a rate sufficient to produce the desired amount of 5tBuMX while minimizing undesirable side reactions. Effective rate will vary depending upon the operating conditions, size, and shape of the reactor. Effective rate will also depend upon the quantity of metaxylene in the reactor and upon the method used to introduce the alkylating agent into the reactor. Effective rate will be greater if greater quantities of metaxylene and clay catalyst are used, however, dispersion of the alkylating agent will be a limiting factor for increase in effective rate. By reducing localized concentrations of alkylating agent, dispersion of the alkylating agent reduces occurrence of side reactions when compared to introducing an alkylating agent without appreciable dispersion. In general, the effective rate will be greater if the alkylating agent is well dispersed when compared to the effective rate when the alkylating agent is poorly dispersed. Dispersion methods can include using multiple sites to add the alkylating agent, using dispersion apparatus such as a multi-ring disperser, or any method or apparatus capable of reducing localized concentrations of the alkylating agent.

The effective rate for adding the alkylating agent is specified relative to the amount of metaxylene in the reactor. For typical commercial operations, the effective rate should be no greater than about 0.35 g/min for every 100 g of metaxylene in the reactor. Preferably, the effective rate is in the range of from about 0.11 g/min to about 0.35 g/min for every 100 g of metaxylene in the reactor. More preferably the effective rate is from about 0.13 g/min to about 0.29 g/min for every 100 g of metaxylene in the reactor. The reactor contents can be mixed to improve the alkylation reaction and decrease oligomerization of alkylating agent molecules.

A reaction product stream is removed from the reactor. The clay catalyst is separated from the reaction product stream through known separation methods such as filtration, centrifuge or any combination of separation methods. A portion of the separated clay catalyst is recycled to the clay catalyst feed. The amount of clay catalyst recycled is determined by the desired percentage of recycled clay catalyst in the clay catalyst feed. Recycled clay catalyst is slightly less effective in the alkylation reaction than fresh clay catalyst. However, the slightly reduced effectiveness of recycled clay catalyst must be weighed against the goals of reduced waste and commercial feasibility. The clay catalyst feed typically comprises more than about 50% wt recycled clay catalyst. Preferably the clay catalyst feed comprises more than about 70% wt recycled clay catalyst. Most preferably the clay catalyst feed comprises from about 90% wt to about 95% wt recycled clay catalyst.

The catalyst-free product stream is fed to a metaxylene recovery tower. In the metaxylene recovery tower, metaxylene and light byproducts are separated from a stream comprising 5tBuMX, 4tBuMX and heavy byproducts. In a typical metaxylene recovery tower, metaxylene and light byproducts are taken overhead where, after cooling and separation, the light byproducts are flared and all or a portion of the metaxylene is recycled to the metaxylene feed. The amount of metaxylene recycled is determined by the desired percentage of recycled metaxylene in the metaxylene feed. Use of recycled metaxylene results in more byproducts from the alkylation reaction. However, increased production of byproducts must be weighed against the goals of reduced waste and commercial feasibility. The metaxylene feed typically comprises more than about 20% wt recycled metaxylene. Preferably the metaxylene feed comprises more than about 40% wt recycled metaxylene. Most preferably the metaxylene feed comprises about 60% wt recycled metaxylene.

The bottoms of the metaxylene recovery tower contain 5tBuMX, some 4tBuMX, and heavy byproducts formed by side reactions. The bottoms are fed to a tBuMX recovery column where heavy byproducts are separated from 5tBuMX and 4tBuMX. Heavy byproducts are sent to disposal. The remaining stream contains 5tBuMX with some 4tBuMX, typically less than about 3 wt % 4tBuMX. One significant advantage of this process is that very little 4tBuMX is produced. If desired, the remaining stream can be further purified by methods commonly employed in the art. This continuous process allows the commercial use of a solid clay catalyst for the production of 5tBuMX by producing a more environmentally benign waste when compared with currently used methods for producing 5tBuMX. This continuous process also reduces the amount of waste while still producing sufficient quantity and quality of 5tBuMX.

Figure 2:
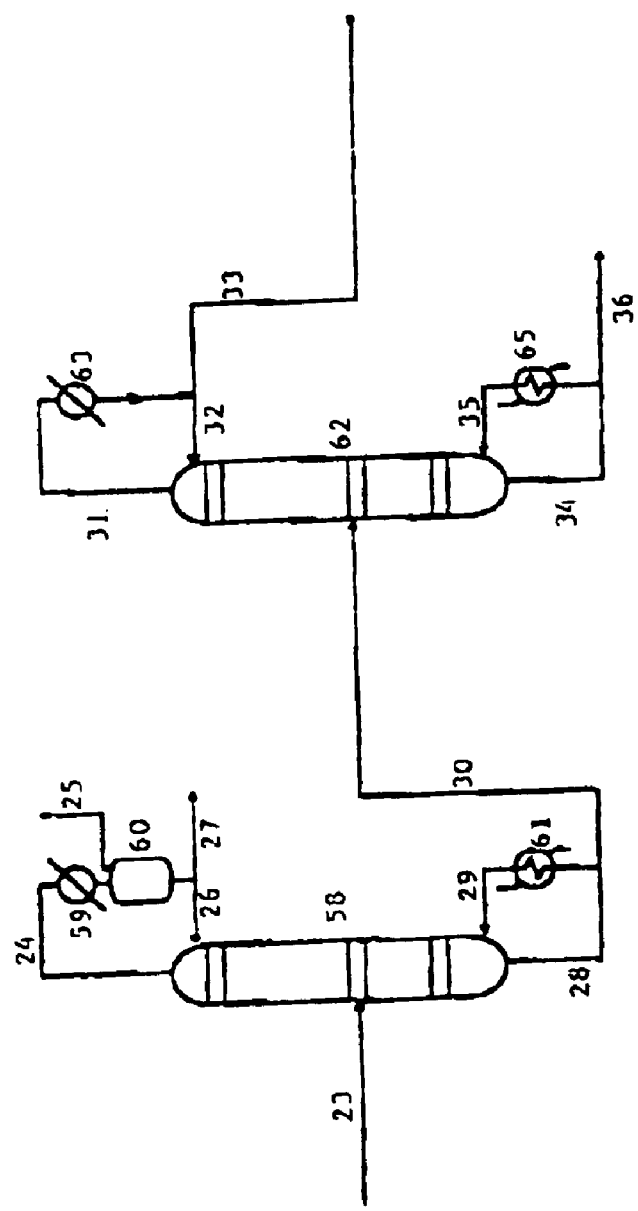

FIGS. 1 and 2 illustrate one embodiment of this invention. In FIG. 1, a metaxylene feed 11 is dehydrated by passing through a dehydration column 51. The dried metaxylene feed 12 is mixed with a clay catalyst feed 13 in a mixer 52 to form a slurry. A slurry stream 14 from the mixer 52 is fed into an alkylation reactor 53. An alkylating agent 15 is sparged into the bottom of the alkylation reactor 53 and stirred. A reaction product stream 18 is removed from the alkylation reactor 53 and cooled using a heat exchanger 55. An overhead gas stream 16 from the alkylation reactor 53 is fed to a knock-back condenser 54 to condense the vapors in the overhead gas stream 16 and return the condensed vapors to the alkylation reactor 53. The remaining gas in the overhead gas stream 16 is sent via line 17 to an incinerator (not shown).

The cooled reaction product stream 19 is fed to a centrifuge 56 where substantially all of the clay catalyst is removed 20. A portion of the removed clay catalyst is recycled and the remainder is sent to disposal (not shown).

The substantially catalyst-free product stream 21 is passed through a filtration unit 57 where the remaining catalyst fines are removed 22.

The catalyst-free product stream 23 is then purified as illustrated in FIG. 2. The catalyst-free product stream 23 is sent to a metaxylene recovery tower 58. Metaxylene and light by products are taken as overhead gases 24 from the metaxylene recovery tower 58. The overhead gases are cooled in a cooling unit 59 and separated in a separation column 60 from which used metaxylene is extracted, a portion of which is returned 26 to the metaxylene recovery column. The remaining used metaxylene 27 is combined with fresh metaxylene to form the metaxylene feed stream 11. A portion of the bottoms 28 of the metaxylene recovery column 58 are passed through a heat exchanger 61 and returned 29 to the metaxylene recovery tower 58. The remainder of the bottoms are fed 30 to a tBuMX recovery column 62.

A portion the bottoms 34 from the tBuMX recovery column 62 are passed through a heat exchanger 65 and returned 35 to the to the tBuMX recovery column 62. The remainder of the bottoms from the tBuMX recovery column 62 are sent 36 to disposal (not shown). The overhead stream 31 taken from the tBuMX recovery column 62 is passed through a cooling unit 63 and a portion is returned 32 to the tBuMX recovery column. The final product stream 33 comprises primarily 5tBuMX with less than 3% wt 4tBuMX.

EXAMPLES

The following examples are illustrative of the process of the present invention. Unless otherwise noted, in the following examples all percentages are by weight and all temperatures are in degrees Celsius.

Comparative Example I

Comparative Example I demonstrates the rapid deactivation of the clay catalyst when used in accordance with the teachings of Fujita et al. A tared 500 ml, three-necked flask equipped with an overhead stirrer, a condenser, and a gas delivery tube is charged with 17.5 g of F-24 catalyst (from Englehard) which has been dried at 110° C. for several hours, and 200 g metaxylene. After the mixture is brought to 130° C., 62–68 g of isobutylene is added at rate of about 0.6 g/min for about 100 minutes. The reaction is allowed to cool, and the flask and its contents are weighed. Samples are removed for analysis by gas chromatography.

TABLE I

| Number of times catalyst is reused | Metaxylene Conversion | 5tBuMX selectivity (Metaxylene) | % 5tBuMX of total tBuMX |
|---|---|---|---|
| 0 | 49% | 97% | 99.7% |
| 1 | 43% | 92% | 98.4% |
| 2 | 23% | 83% | 91% |
| 3 | 8% | 78% | 86% |

Comparative Example I shows rapid deactivation of the clay catalyst when practiced in accordance with the prior art.

Examples 1 and 2 demonstrate the extended catalyst lifetime achieved by the instant invention.

Example 1

A 1 liter stainless steel autoclave is charged with 35 g of F-24 catalyst which has been dried at 100° C. for 8 hours, and 400 g of metaxylene. The pressure is raised to about 50 psig with nitrogen. The mixture is stirred and heated to 150° C. isobutylene is added at a fixed rate of 0.62 g/min with an ISCO pump to maintain a steady delivery of gas over the 100 minute reaction time. Upon cooling, the mixture is drained into a vessel, weighed, and a sample removed for analysis. The catalyst is removed by filtration and recycled for another run.

TABLE 1

| Number of times catalyst is reused | Metaxylene Conversion | 5tBuMX selectivity (Metaxylene) | % 5tBuMX of total tBuMX |
|---|---|---|---|
| 0 | 23% | 92% | 98% |
| 1 | 24% | 90% | 98% |
| 2 | 23% | 90% | 98% |
| 3 | 24% | 89% | 98% |
| 4 | 23% | 89% | 97% |
| 5 | 22% | 89% | 99% |
| 6 | 22% | 88% | 97% |
| 7 | 19% | 89% | 97% |
| 8 | 19% | 91% | 98% |
| 9 | 21% | 89% | 97% |
| 10 | 22% | 88% | 97% |

Example 2

A 1 liter stainless steel autoclave was modified so that the catalyst was not removed between runs. A dip leg was added to allow removal of the reaction products. Fresh metaxylene for each run was added through the dip tube. The reactor temperature was maintained near 135° C. as indicated in Table 2. The reactor is initially charged with 45 g of F-24 catalyst which has been dried at 100° C. for 8 hours. The amount of metaxylene indicated in Table 2 is added. The pressure is raised with nitrogen to the level indicated in Table 2. The mixture is stirred, isobutylene is added at a fixed rate with an ISCO pump to maintain a steady delivery of gas over the reaction time. The reaction products are removed, but the catalyst remains in the reactor. Fresh metaxylene is added for another run.

As shown by examples 1 and 2, in the process of this invention, the catalyst life is significantly extended.

Example 3

A 1 liter stainless steel autoclave reactor was modified so that the catalyst was not removed between runs. A dip leg was added to allow removal of the reaction products. Metaxylene for each run was added through the dip tube. The reactor temperature was maintained near 135° C. as indicated in Table 3. The reactor is initially charged with 45 g of F-24 catalyst which has been dried at 100° C. for 8 hours. The amount of metaxylene indicated in Table 3 is added. The pressure is raised with nitrogen to the level indicated in Table 3. The mixture is stirred. Isobutylene is added at a fixed rate with an ISCO pump to maintain a steady delivery of gas over the reaction time. The reaction products are removed, but the catalyst remains in the reactor. After the initial run, the metaxylene added is about 40% fresh metaxylene and 60% recycled metaxylene. Recycled metaxylene was generated by distilling the previous run products through a 12" long 5 tray vacuum jacketed Oldershaw column.

TABLE 2

| Temperature (° C.) | Pressure (psig) | Metaxylene (g) | Isobutylene (g) | Isobutylene Addition Rate (g/min.) | Metaxylene Conversion (%) | % 5tBuMX selectivity (Metaxylene) | % 5tBuMX of total tBuMX |
|---|---|---|---|---|---|---|---|
| 133 | 72 | 424 | 57 | 0.63 | 20.14 | 99.05 | 99.99 |
| 134 | 63 | 375 | 57 | 0.63 | 29.75 | 98.34 | 99.96 |
| 134 | 59 | 393 | 57 | 0.63 | 27.66 | 97.86 | 99.98 |
| 132 | 63 | 424 | 57 | 0.63 | 26.18 | 98.54 | 99.99 |
| 131 | 59 | 424 | 57 | 0.63 | 23.56 | 98.70 | 99.99 |
| 134 | 68 | 424 | 58 | 0.63 | 24.18 | 98.62 | 99.99 |
| 134 | 99 | 424 | 58 | 0.63 | 21.87 | 98.43 | 99.99 |
| 135 | 63 | 424 | 57 | 0.63 | 24.27 | 98.55 | 99.99 |
| 134 | 68 | 424 | 58 | 0.63 | 23.31 | 98.64 | 99.99 |
| 135 | 66 | 424 | 57 | 0.63 | 24.35 | 98.61 | 99.99 |
| 136 | 59 | 424 | 57 | 0.63 | 26.95 | 98.26 | 99.98 |
| 135 | 63 | 424 | 57 | 0.63 | 23.39 | 98.55 | 99.99 |

TABLE 3

| Temperature (° C.) | Pressure (psig) | Metaxylene (g) | Isobutylene (g) | Isobutylene Addition Rate (g/min.) | Metaxylene Conversion (%) | % 5tBuMX selectivity (Metaxylene) | % 5tBuMX of total tBuMX |
|---|---|---|---|---|---|---|---|
| 136 | 72 | 424 | 57 | 0.63 | 24.64 | 98.99 | 99.98 |
| 134 | 63 | 424 | 57 | 0.63 | 24.29 | 98.86 | 99.98 |
| 135 | 67 | 424 | 58 | 0.63 | 25.12 | 98.32 | 99.99 |
| 134 | 61 | 424 | 57 | 0.63 | 23.27 | 98.06 | 99.99 |
| 135 | 67 | 424 | 58 | 0.63 | 24.67 | 98.36 | 99.99 |
| 133 | 69 | 424 | 58 | 0.63 | 23.53 | 98.25 | 99.99 |
| 134 | 60 | 424 | 58 | 0.63 | 23.73 | 97.73 | 99.98 |
| 134 | 55 | 424 | 58 | 0.63 | 23.67 | 97.77 | 99.99 |
| 134 | 68 | 424 | 58 | 0.63 | 23.45 | 97.55 | 99.98 |

TABLE 3-continued

| Temperature (° C.) | Pressure (psig) | Metaxylene (g) | Isobutylene (g) | Isobutylene Addition Rate (g/min.) | Metaxylene Conversion (%) | % 5tBuMX selectivity (Metaxylene) | % 5tBuMX of total tBuMX |
|---|---|---|---|---|---|---|---|
| 133 | 73 | 424 | 58 | 0.63 | 23.61 | 97.07 | 99.98 |
| 134 | 62 | 424 | 58 | 0.63 | 23.71 | 96.35 | 99.97 |
| 133 | 62 | 424 | 57 | 0.63 | 21.88 | 95.89 | 99.97 |
| 133 | 69 | 424 | 57 | 0.63 | 21.18 | 95.92 | 99.95 |
| 134 | 62 | 424 | 57 | 0.63 | 24.01 | 95.52 | 99.94 |
| 132 | 66 | 424 | 57 | 0.63 | 21.76 | 94.63 | 99.94 |
| 134 | 67 | 424 | 58 | 0.63 | 23.01 | 94.60 | 99.93 |
| 134 | 62 | 424 | 57 | 0.63 | 22.60 | 94.21 | 99.92 |
| 135 | 61 | 424 | 58 | 0.63 | 23.09 | 93.83 | 99.89 |
| 134 | 61 | 424 | 58 | 0.63 | 20.13 | 93.68 | 99.90 |
| 134 | 63 | 424 | 58 | 0.63 | 19.96 | 92.60 | 99.84 |
| 134 | 63 | 424 | 57 | 0.63 | 19.27 | 93.38 | 99.91 |

While the invention has been illustrated by means of specific embodiments, these are not intended to be limiting. Further additions and modifications will be readily apparent to those skilled in the art, and such modifications, formulations and articles embodying them, are contemplated to lie within the scope of the invention as defined and set forth in the following claims.

That which is claimed is:

1. A process to produce 5-tert-butyl-metaxylene comprising:
  a) adding a suitable alkylating agent to a mixture comprising active clay catalyst, a pressure-maintaining amount of non-reactive gas, and an effective amount of metaxylene into a reactor at reaction conditions comprising a temperature of at least 125° C. and a pressure of at least 450 kPa at an alkylating agent addition rate effective to form 5-tert-butyl-metaxylene;
  b) recovering a portion of the 5-tert-butyl-metaxylene and a portion of the metaxylene without removal of the active clay catalyst from the reactor;
  c) separating the 5-tert-butyl-metaxylene from the metaxylene;
  d) recycling at least a portion of the separated metaxylene to the reactor.

2. The process to produce 5-tert-butyl-metaxylene of claim 1, wherein the active clay catalyst is an active dioctahedral smectite clay.

3. The process to produce 5-tert-butyl-metaxylene of claim 1, wherein the weight ratio of metaxylene to active clay catalyst in the mixture is greater than about 4:1.

4. The process to produce 5-tert-butyl-metaxylene of claim 1, wherein the alkylating agent addition rate is less than about 0.35 g/min for every 100 g of metaxylene in the mixture.

5. The process to produce 5-tert-butyl-metaxylene of claim 1, wherein the alkylating agent is isobutylene.

6. A process to produce 5-tert-butyl-metaxylene comprising:
  a) adding a suitable alkylating agent to a mixture comprising active clay catalyst, a pressure-maintaining amount of non-reactive gas, and an effective amount of metaxylene into a reactor at reaction conditions comprising a temperature of at least 125° C. and a pressure of at least 450 kPa at an alkylating agent addition rate effective to form 5-tert-butyl-metaxylene;
  b) recovering a portion of the 5-tert-butyl-metaxylene, a portion of the metaxylene, and a portion of the active clay catalyst from the reactor;
  c) separating the 5-tert-butyl-metaxylene from the recovered metaxylene and recovered active clay catalyst; and
  d) recycling at least a portion of the recovered active clay catalyst and at least a portion of the recovered metaxylene to the reactor.

7. The process to produce 5-tert-butyl-metaxylene of claim 6, wherein the active clay catalyst is an active dioctahedral smectite clay.

8. The process to produce 5-tert-butyl-metaxylene of claim 6, wherein the weight ratio of metaxylene to active clay catalyst in the mixture is greater than about 4:1.

9. The process to produce 5-tert-butyl-metaxylene of claim 6, wherein the alkylating agent addition rate is less than about 0.35 g/min for every 100 g of metaxylene in the mixture.

10. The process to produce 5-tert-butyl-metaxylene of claim 6, wherein the alkylating agent is isobutylene.

11. A process to produce 5-tert-butyl-metaxylene comprising:
  a) adding a suitable alkylating agent to a mixture comprising active clay catalyst, a pressure-maintaining amount of non-reactive gas, and an effective amount of metaxylene into a reactor at reaction conditions comprising a temperature of from about 131° C. to about 156° C. and a pressure of from about 515 kPa to about 620 kPa at an alkylating agent addition rate of from about 0.11 g/min to about 0.35 g/min for every 100 g of metaxylene in the reactor;
  b) recovering a portion of the 5-tert-butyl-metaxylene, a portion of the metaxylene, and a portion of the active clay catalyst from the reactor;
  c) separating the 5-tert-butyl-metaxylene from the recovered metaxylene and recovered active clay catalyst; and
  d) recycling at least a portion of the recovered active clay catalyst and at least a portion of the recovered metaxylene to the reactor.

12. The process to produce 5-tert-butyl-metaxylene of claim 11, wherein the active clay catalyst is an active dioctahedral smectite clay.

13. The process to produce 5-tert-butyl-metaxylene of claim 11, wherein the alkylating agent is isobutylene.

14. The process to produce 5-tert-butyl-metaxylene of claim 11, wherein the weight ratio of metaxylene to active clay catalyst in the mixture is about 9:1.

15. The process to produce 5-tert-butyl-metaxylene of claim 11, wherein the reactor pressure is about 585 psig.

16. The process to produce 5-tert-butyl-metaxylene of claim 11, wherein the alkylating agent addition rate is from about 0.13 g/min to about 0.29 g/min for every 100 g of metaxylene in the mixture.

17. The process to produce 5-tert-butyl-metaxylene of claim 11, wherein the active clay catalyst is an active montmorillonite clay.

* * * * *